United States Patent
Uekawa et al.

(10) Patent No.: US 8,048,916 B2
(45) Date of Patent: Nov. 1, 2011

(54) ESTER COMPOUND AND USE THEREOF

(75) Inventors: Toru Uekawa, Toyonaka (JP); Jun Ohshita, Nishinomiya (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 271 days.

(21) Appl. No.: 12/529,559

(22) PCT Filed: Mar. 6, 2008

(86) PCT No.: PCT/JP2008/054560
§ 371 (c)(1),
(2), (4) Date: Sep. 2, 2009

(87) PCT Pub. No.: WO2008/111627
PCT Pub. Date: Sep. 18, 2008

(65) Prior Publication Data
US 2010/0041750 A1  Feb. 18, 2010

(30) Foreign Application Priority Data
Mar. 7, 2007 (JP) ................... 2007-056889

(51) Int. Cl.
*A01N 53/02* (2006.01)
*C07C 69/74* (2006.01)
*A01P 15/00* (2006.01)

(52) U.S. Cl. ...................... 514/531; 560/124
(58) Field of Classification Search .................. None
See application file for complete search history.

(56) References Cited

U.S. PATENT DOCUMENTS

| | | |
|---|---|---|
| 4,405,640 A | 9/1983 | Punja |
| 4,565,822 A | 1/1986 | Tessier et al. |
| 5,135,951 A | 8/1992 | Babin et al. |
| 5,192,801 A | 3/1993 | Babin et al. |

FOREIGN PATENT DOCUMENTS

JP  2002-212138 A  7/2002

*Primary Examiner* — Kamal Saeed
(74) *Attorney, Agent, or Firm* — Panitch Schwarze Belisario & Nadel LLP

(57) ABSTRACT

A compound represented by the formula (I):

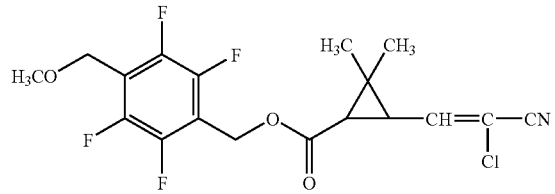

(I)

has an excellent pest controlling activity and therefore is useful for an effective ingredient of a pest control composition.

3 Claims, No Drawings

ESTER COMPOUND AND USE THEREOF

CROSS-REFERENCE TO RELATED APPLICATION

This application is a Section 371 of International Application No. PCT/JP2008/054560, filed Mar. 6, 2008, which was published in the English language on Sep.18, 2008 under International Publication No. WO 2008/111627 A1, and the disclosure of which is incorporated herein by reference.

TECHNICAL FIELD

The present invention relates to an ester compound and use thereof.

BACKGROUND ART

U.S. Pat. Nos. 5,135,951 and 5,192,801 disclose a certain kind of 2,2-dimethyl-3-(2-halo-2-cyanovinyl)cyclopropane carboxylate compounds.

DISCLOSURE OF THE INVENTION

An object of the present invention is to provide a compound having an excellent pest control effect.

The present inventors have studied intensively to find out a cyclopropane carboxylate compound having an excellent pest control effect and, as a result, they have found that a compound represented by the following formula (I) has an excellent pest control effect. Thus, the present invention has been completed.

That is, the present invention provides:
(1) An ester compound represented by the formula (I):

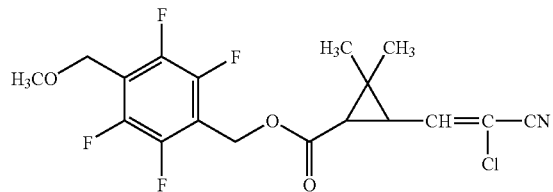

(hereinafter referred to as the compound of the present invention);
(2) A pest control composition comprising an ester compound represented by the formula (I);
(3) A pest control method which comprises applying an effective amount of an ester compound represented by the formula (I) to pests or a habitat of pests;
(4) Use of an ester compound represented by the formula (I) for controlling pests; and
(5) Use of an ester compound represented by the formula (I) for manufacturing a pest controlling composition.

BEST MODE FOR PERFORMING THE INVENTION

The compound of the present invention includes an isomer derived from two asymmetric carbon atoms existing on the cyclopropane ring and an isomer derived from the double bond. The present invention includes each of the isomers and a mixture thereof having any ratio thereof.

Specific examples of the compound of the present invention are as follows:

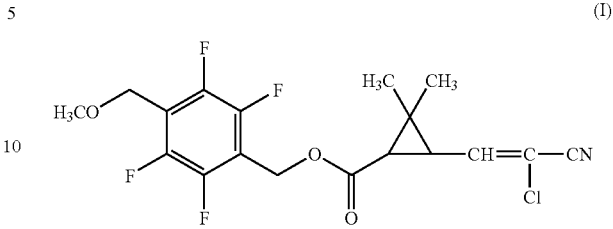

The ester compound of the above-mentioned formula (I), wherein the absolute configuration at 1-position of the cyclopropane ring is R configuration;

The ester compound of the above-mentioned formula (I), wherein the relative configuration between the substituent at 1-position of the cyclopropane ring and the substituent at 3-position of the cyclopropane ring is trans configuration;

The ester compound of the above-mentioned formula (I), wherein the relative configuration between the substituent at 1-position of the cyclopropane ring and the substituent at 3-position of the cyclopropane ring is cis configuration;

The ester compound of the above-mentioned formula (I), wherein the relative configuration between the carbon-carbon double bond existing in the substituent at 3-position of the cyclopropane ring is E configuration;

The ester compound of the above-mentioned formula (I), wherein the absolute configuration at 1-position of the cyclopropane ring is R configuration, and the relative configuration between the substituent at 1-position of the cyclopropane ring and the substituent at 3-position of the cyclopropane ring is trans configuration;

The ester compound of the above-mentioned formula (I), wherein the absolute configuration at 1-position of the cyclopropane ring is R configuration, and the relative configuration between the substituent at 1-position of the cyclopropane ring and the substituent at 3-position of the cyclopropane ring is cis configuration;

The ester compound of the above-mentioned formula (I), wherein the absolute configuration at 1-position of the cyclopropane ring is R configuration, and the relative configuration between the substituent at 1-position of the cyclopropane ring and the substituent at 3-position of the cyclopropane ring is trans configuration, and the relative configuration between the carbon-carbon double bond existing in the substituent at 3-position of the cyclopropane ring is E configuration;

The ester compound of the above-mentioned formula (I), wherein the absolute configuration at 1-position of the cyclopropane ring is R configuration, and the relative configuration between the substituent at 1-position of the cyclopropane ring and the substituent at 3-position of the cyclopropane ring is rich in trans configuration;

The ester compound of the above-mentioned formula (I), wherein the absolute configuration at 1-position of the cyclopropane ring is R configuration, and 80% or more of the relative configuration between the substituent at 1-position of the cyclopropane ring and the substituent at 3-position of the cyclopropane ring is trans configuration; and The ester compound of the above-mentioned formula (I), wherein the absolute configuration at 1-position of the cyclopropane ring is R configuration, and 90% or more of the relative configuration between the substituent at 1-position of the cyclopropane ring and the substituent at 3-position of the cyclopropane ring is with trans configuration.

The compound of the present invention can be produced by, for example, the following Production Process 1.

Production Process 1

A process comprising reacting an alcohol compound represented by the formula (II):

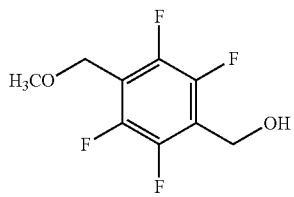

(II)

with a carboxylic acid represented by the formula (III):

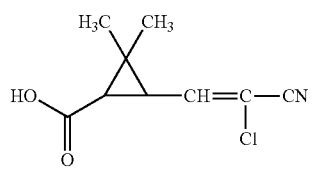

(III)

or a reactive derivative thereof (e.g., acid halide and acid anhydride, etc.).

The reaction is usually performed in a solvent in the presence of a condensing agent or a base.

Examples of the condensing agent include dicyclohexylcarbodiimide and 1-ethyl-3-(3-dimethylaminopropyl)carbodiimide hydrochloride.

Examples of the base include organic bases such as triethylamine, pyridine, N,N-diethylaniline, 4-dimethylaminopyridine and diisopropylethylamine.

Examples of the solvent include hydrocarbons such as benzene, toluene and hexane, ethers such as diethyl ether and tetrahydrofuran, and halogenated hydrocarbons such as dichloromethane, 1,2-dichloroethane and chlorobenzene. A mixture of these solvents can also be used.

The reaction time is generally in the range of 5 minutes to 72 hours.

The reaction temperature is generally in the range of $-20$ to $100°$ C. (however, in the case where the boiling point of a solvent to be used is less than $100°$ C., $-20°$ C. to the boiling point of the solvent), preferably in the range of $-5$ to $100°$ C. (however, in the case where the boiling point of a solvent to be used is less than $100°$ C., $-5°$ C. to the boiling point of the solvent).

In the reaction, the molar ratio of the alcohol compound represented by the formula (II) and the carboxylic acid compound represented by the formula (III) or a reactive derivative thereof to be used can be appropriately selected. Preferably, equimolar or a close ratio thereto can be selected. Specifically, 0.5 to 3 mol of the carboxylic acid compound represented by the formula (III) or a reactive derivative thereof is preferably used relative to 1 mol of the alcohol compound represented by the formula (II).

The condensing agent or the base can be used usually at an appropriate ratio selected from 1 mol to excessive amount, preferably 1 to 5 mol, relative to 1 mol of the alcohol compound represented by the formula (II). The condensing agent or the base are appropriately selected depending on a particular kind of the carboxylic acid compound represented by the formula (III) or a reactive derivative thereof (e.g., corresponding acid chloride compounds, acid bromide compounds, acid anhydrides, etc.).

After completion of the reaction, the compound of the present invention can be isolated from a reaction mixture by conventional post-treatment, for example, by pouring water, extracting with an organic solvent and concentration. The compound of the present invention compound thus isolated can further be purified by, for example, chromatography, distillation, and the like.

The alcohol compound represented by the formula (II) is described, for example, in U.S. Pat. No. 4,405,640 and can be produced by the process described therein.

The carboxylic acid compound represented by the formula (III) is described, for example, in U.S. Pat. No. 4,565,822 and can be produced by the process described therein.

The compound of the present invention can also be produced by the following Production Process 2.

Production Process 2

A process comprising reacting an aldehyde compound represented by the formula (IV):

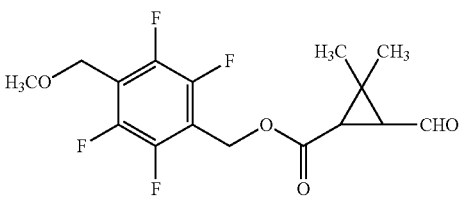

(IV)

with a phosphonate compound represented by the formula (V):

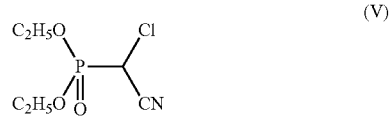

(V)

The reaction is usually performed in a solvent in the presence of a base.

Examples of the base include alkali metal alkoxides such as sodium methoxide and potassium tert-butoxide, alkali metal hydrides such as sodium hydride and potassium hydride, and alkali metal amides such as sodium bistrimethylsilylamide, lithium bistrimethylsilylamide and lithium diisopropylamide.

Examples of the solvent include hydrocarbons such as benzene, toluene and hexane, and ethers such as diethyl ether and tetrahydrofuran. A mixture of these solvents can also be used.

The reaction time is generally in the range of 5 minutes to 72 hours.

The reaction temperature is generally in the range of $-80$ to $100°$ C. (however, in the case where the boiling point of a solvent to be used is less than $100°$ C., $-80°$ C. to the boiling point of the solvent).

In the reaction, a molar ratio of then aldehyde compound represented by the formula (IV) and the phosphonate compound represented by the formula (V) to be used can be appropriately selected. Preferably, equimolar or close ratio thereto can be selected. Specifically, 0.5 to 3 mol of the phosphonate compound represented by the formula (V) is preferably used relative to 1 mol of the aldehyde compound represented by the formula (IV).

The base can be used usually at an appropriate ratio selected from 1 mol to an excessive amount, preferably 1 to 5 mol, relative to 1 mol of the phosphonate compound represented by the formula (V).

After completion of the reaction, the compound of the present invention can be isolated from a reaction mixture by conventional post-treatment, for example, by pouring water, extracting with an organic solvent and concentration. The compound of the present invention compound thus isolated can further be purified by, for example, chromatography, distillation, and the like.

The aldehyde compound represented by the formula (IV) is described, for example, in JP 2002-212138 A and can be produced by the process described therein.

The compound represented by the formula (V) is described in J. Chem. Soc., Perkin Trans. 1, 19, 3311 (2000) and can be produced by the process described therein.

Examples of pests on which the compound of the present invention has effect include arthropods such as insects and ticks, and specific examples thereof are as follows.

Lepidoptera:
Pyralidae such as *Chilo suppressalis* (rice stem borer), *Cnaphalocrocis medinalis* (rice leafroller), *Plodia interpunctella* (Indian meal moth) and the like; Noctuidae such as *Spodoptera litura* (common cutworm), *Pseudaletia separata* (rice armyworm), *Mamestra brassicae* (cabbage armyworm) and the like; Pieridae such as *Pieris rapae* (common cabbageworm) and the like; Tortricidae such as *Adoxophyes orana* and the like; Carposinidae; Lyonetiidae; Lymantriidae; Autographa; *Agrotis* spp. such as *Agrotis segetum* (cutworm), *Agrotis ipsilon* (black cutworm) and the like; *Helicoverpa* spp.; *Heliothis* spp.; *Plutella xylostella* (diamondback moth); *Parnara guttata* (rice skipper); *Tinea translucens* (casemaking clothes moth); *Tineola bisselliella* (webbing clothes moth); and the like;

Diptera:
Calicidae such as *Culex pipiens pallens* (common mosquito), *Culex tritaeniorhynchus*, and the like; *Aedes* spp. such as *Aedes aegypti*, *Aedes albopictus* and the like; *Anopheles* such as *Anopheles sinensis* and the like; Chironomidae (midges); Muscidae such as *Musca domestica* (housefly), *Muscina stabulans* (false stablefly), Fanniidae and the like; Calliphoridae; Sarcophagidae; Anthomyiidae such as *Delia platura* (seedcorn maggot), *Delia antiqua* (onion maggot) and the like; Tephritidae (fruit flies); Drosophilidae (small ruit flies); Psychodidae (moth flies); Phoridae; Tabanidae; Simuliidae (black flies); Stomoxyidae (stable flies); Ceratopogonidae; and the like;

Blattodea:
*Blattella germanica* (German cockroach), *Periplaneta fuliginosa* (smokybrown cockroach), *Periplaneta americana* (American cockroach), *Periplaneta brunnea* (brown cockroach), *Blatta orientalis* (oriental cockroach) and the like;

Hymenoptera:
Formicidae (Ants); Vespidae (hornets); Bethylid wasp; Tenthredimidae such as *Athalia rosae ruficornis*, and the like;

Aphaniptera:
*Ctenocephalides canis*, *Ctenocephalides felis*, *Pulex irritans* and the like;

Anoplura:
*Pediculus humanus*, *Phthirus pubis*, *Pediculus humanus humanus*, *Pediculus humanus corporis* and the like;

Isoptera:
*Reticulitermes speratus*, *Coptotermes formosanus*, and the like;

Hemiptera:
Delphacidae (planthoppers) such as *Laodelphax striatellus* (small brown planthopper), *Nilaparvata lugens* (brown rice planthopper), *Sogatella furcifera* (white-backed rice planthopper) and the like; Deltocephalidae (leafhoppers) such as *Nephotettix cincticeps* (green rice leafhopper), *Nephotettix virescens* (green rice leafhopper) and the like; Aphididae (aphids); Pentatomidae (stink bugs); Aleyrodidae (whiteflies); Coccidae (scales); Tingidae (lace bugs); Psyllidae (psyllids), and the like;

Coleoptera:
*Attagenus japonicus*; *Anthrenus verbasci*; *Diabrotica* spp. (corn rootworms) such as *Diabrotica virgifera* (western corn rootworm), *Diabrotica undecimpunctata howardi* (southern corn rootworm) and the like; Scarabaeidae such as *Anomala cuprea* (cupreous chafer), *Anomala rufocuprea* (soybeans beatle) and the like; Curculionidae such as *Sitophilus zeamais* (maize weevil), *Lissorhoptrus oryzophilus* (rice water weevil), *Anthonomus gradis grandis* (cottonseed weevil), *Callosobruchuys chienensis* (adzuki been weevil) and the like; Tenebrionidae (darkling beetles) such as *Tenebrio molitor* (yellow mealworm), *Tribolium castaneum* (red flour beetle) and the like; Chrysomelidae (leaf beetles) such as *Oulema oryzae* (rice leaf beetles), *Phyllotreta striolata* (striped flea beetle), *Aulacophora femoralis* (cucurbit leaf beetle), and the like; Anobiidae (drugstore beetles); *Epilachna* spp. such as *Epilachna vigintioctopunctata* (twenty-eight-spotted ladybird) and the like; Lyctidae (powder post beetles); Bostrychidae (false powder post beetles); Cerambycidae (longhorn beetles); *Paederus fuscipes* (rove beetles); and the like;

Thysanoptera:
*Thrips palmi*, *Frankliniella occidentalis*, *Thrips hawaiiensis* (flower thrips) and the like;

Orthoptera:
Gryllotalpidae, Acrididae (grasshopper), and the like;

Acarina:
Epidermoptidae such as *Dermatophagoides farinae*, *Dermatophagoides ptrenyssnus* and the like; Acaridae such as *Tyrophagus putrescentiae* (mold mite), *Aleuroglyphus ovatus* (brown legged grain mite) and the like; Glycyphagidae such as *Glycyphagus privatus*, *Glycyphagus domesticus*, *Glycyphagus destructor* (groceries mite) and the like; Cheyletidae such as *Cheyletus malaccensis*, *Cheyletus fortis* and the like; Tarsonemidae; Chortoglyphidae; Haplochthoniidae; Tetranychidae such as *Tetranychus urticae* (two-spotted spider mite), *Tetranychus kanzawai* (Kanzawa spider mite), *Panonychus citri* (citrus red mite), *Panonychus ulmi* (European red mite) and the like; and Ixodidae such as *Haemaphysalis longicornis* and the like.

The compound of the present invention itself may be used as a pest control agent but, usually, the compound of the present invention is formulated as an effective ingredient in a pest control composition.

Examples of the pest control composition include an oil-based formulation, an emulsion, a wettable powder, a flowable formulation (such as an aqueous suspension and an aqueous emulsion), a dusting powder, granules, an aerosol spray formulation, a volatile formulation by heating (such as an insecticidal coil, an insecticidal mat for electric heating and a volatile formulation with absorptive wick for heating), a thermal fumigant (such as a self burning type fumigant, a chemical reaction type fumigant and a porous ceramic plate fumigant), a non-heating volatile formulation (such as a resin volatile formulation and an impregnated paper volatile formulation), a smoking formulation (such as fogging), a ULV formulation, and poison bait.

Examples of a formulating method of the pest control composition include following methods.

(1) A method for mixing the compound of the present invention with a solid carrier, a liquid carrier, a gaseous carrier or bait, and if necessary adding a surfactant and other formulation auxiliaries thereto.

(2) A method for impregnating the compound of the present invention into a base material containing no effective ingredient.

(3) A method for mixing the compound of the present invention with a base material, and optionally adding a surfactant and other auxiliaries for preparation, and then molding.

Usually, the pest control composition can contain the compound of the present invention in an amount ranging from 0.001 to 95% by weight depending on its particular form.

Examples of the carrier used for formulating the pest control composition include solid carriers (such as clays (such as kaoline clay, diatomaceous earth, synthetic hydrated silicon oxide, bentonite, Fubasami clay and acid clay), talc, ceramic, other inorganic minerals {such as sericite, quartz, sulfur, activated carbon, calcium carbonate, hydrated silica and montmorillonite) and chemical fertilizers (such as ammonium sulfate, ammonium phosphate, ammonium nitrate, urea and ammonium chloride), liquid carriers {such as water, alcohols (such as methanol and ethanol), ketones (such as acetone and methyl ethyl ketone), aromatic hydrocarbons (such as benzene, toluene, xylene, ethylbenzene, methylnaphthalene and phenylxylylethane), aliphatic hydrocarbons (such as hexane, cyclohexane, kerosene and light oil), esters (such as ethyl acetate and butyl acetate), nitriles (such as acetonitrile and isobutyronitrile), ethers (such as diisopropyl ether and dioxane), acid amides (such as N,N-dimethylformamide and N,N-dimethylacetamide), halogenated hydrocarbons (such as dichloromethane, trichloroethane and carbon tetrachloride), dimethyl sulfoxide and vegetable oils (such as soybean oil and cottonseed oil)}, and gaseous carriers {such as fleon gas, butane gas, LPG (liquefied petroleum gas), dimethyl ether and carbon dioxide gas}.

Examples of the surfactant include alkyl sulfates, alkyl sulfonates, alkylaryl sulfonates, alkylaryl ethers, polyoxyethylated products of alkylaryl ethers, polyethylene glycol ethers, polyhydric alcohol esters and sugar alcohol derivatives.

Examples of other formulation auxiliaries include a fixing agent, a dispersant and a stabilizer such as casein, gelatin, polysaccharides (such as starch, gum arabic, cellulose derivatives and alginic acid), lignin derivatives, bentonite, synthetic water-soluble macromolecules (such as polyvinyl alcohol and polyvinyl pyrrolidone), polyacrylic acids, BHT (2,6-di-tert-butyl-4-methylphenol), and BHA (a mixture of 2-tert-butyl-4-methoxyphenol and 3-tert-butyl-4-methoxyphenol).

Examples of the base material for an insecticidal coil include a mixture of plant powders such as wooden powder and Pyrethrum marc, and binders such as Tabu powder (powder of *Machilus thunbergii*), starch and gluten.

Examples of the base material for an insecticidal mat for electric heating include a plate obtained by hardening cotton linters, and a plate obtained by hardening fibrils of a mixture of cotton linters and pulp.

Examples of a base material for a self burning type fumigant include burning exothermic agents such as nitrate, nitrite, guanidine salt, potassium chlorate, nitrocellulose, ethyl cellulose and wood flour, pyrolytic stimulants such as alkali metal salts, alkaline earth metal salts, dichromates and chromates, oxygen carriers such as potassium nitrate, combustion improvers such as melamine and wheat starch, extenders such as diatomaceous earth, and binders such as synthetic stabilizer.

Examples of the base material for a chemical reaction type fumigant include exothermic agents such as sulfide, polysulfide and hydrosulfide of alkali metals and calcium oxide, catalysts such as carbonaceous material, iron carbide and activated clay, organic forming agents such as azodicarbonamide, benzene sulfonyl hydrazide, dinitropentamethylenetetramine, polystyrene and polyurethane, and fillers such as natural fiber pieces and synthetic fiber pieces.

Examples of the base material for a non-heating volatile preparation include thermoplastic resins and papers such as filter paper and Japanese paper.

Examples of the base material for poison bait include bait ingredients such as grain flour, vegetable oil, sugar and crystalline cellulose, antioxidants such as dibutylhydroxytoluene and nordihydroguaiaretic acid, preservative such as dehydroacetic acid, agents which prevent children and pets from eating by mistake such as powdered capsicum, and vermin attracting perfumes such as cheese perfume, onion perfume and peanut oil.

The pest control method of the present invention is generally performed by applying the pest control composition of the present invention to pests or a habitat of pests.

Examples of the application method of the pest control composition of the present invention include the following methods, which can be appropriately selected according to a particular form, a particular application place of the pest control composition of the present invention, etc.

(1) A method of directly applying the pest control composition of the present invention to pests or a habitat of pests.

(2) A method of applying the pest control composition of the present invention diluted with a solvent such as water to pests or a habitat of pests by spraying.

In this case, usually, the pest control composition of the present invention is formulated in the form of an emulsion, a wettable powder, a flowable type pesticide and microcapsules, and the composition is diluted so that the concentration of the compound of the present invention becomes 0.1 to 10,000 ppm.

(3) A method of heating the pest control composition of the present invention at a habitat of pests to volatilize the effective ingredient thereof.

In this case, the amount and the concentration of the compound of the present invention to be applied can be appropriately determined according to particular form of the composition, application period, application place, application method of the pest control composition of the present invention, as well as particular kind and situation of damage of pests.

The pest control composition of the present invention can also be used by mixture or together with one or more other insecticides, nematicides, soil insect pest control compositions, bactericides, herbicides, plant growth regulators, repellents, synergists, fertilizers and soil conditioners.

Examples of the effective ingredient of such an insecticide and a miticide include organophosphorus compounds such as fenitrothion, fenthion, diazinon, chlorpyrifos, acephate, methidathion, disulfoton, DDVP, sulprofos, cyanophos, dioxabenzophos, dimethoate, phenthoate, malathion, trichlorfon, azinphosmethyl, monocrotophos and ethion, carbamate compounds such as BPMC, benfuracarb, propoxur, carbosulfan, carbaryl, methomyl, ethiofencarb, aldicarb, oxamyl and phenothiocarb, pyrethroid compounds such as ethofenprox, fenvalerate, ethfenvalerate, fenpropathrin, cypermethrin, permethrin, cyhalothrin, deltamethrin, cycloprothrin, fluvalinate, biphenthrin, 2-methyl-2-(4-bromodifluoromethoxyphenyl)propyl(3-phenoxybenzyl)ether, tralomethrin, silafluofen, d-phenothrin, cyphenothrin, d-resmethrin, acrinathrin, cyfluthrin, tefluthrin, transfluthrin, tetramethrin, allethrin, d-furamethrin, prallethrin, empenthrin and 5-(2-propynyl)furfuryl 2,2,3,3-tetramethylcyclopropanecarboxylate, and nitroimidazolidine derivative, N-cyanoamidine derivative such as acetamiprid, chlorinated hydrocarbon compounds such as endosulfan, γ-BHC and 1,1-bis(chlorophenyl)-2,2,2-trichloroethanol, benzoylphenylurea compounds such as chlorfluazuron, teflubenzuron and flufenoxuron, phenylpyrazole compounds, metoxadiazone, bromopropylate, tetradifon, chinomethionate, pyridaben, fenpyroximate, diafenthiuron, tebufenpyrad, polynactin complex [tetranactin, dinactin and trinactin], pyrimidifen, milbemectin, abamectin, ivermectin and azadirachtin.

Examples of the repellent include 3,4-caranediol, N,N-diethyl-meta-toluamide, 1-methylpropyl 2-(2-hydroxyethyl)-1-piperidine carboxylate, para-menthane-3,8-diol and botanical essential oil such as Hyssopus officinalis oil.

Examples of the synergist include bis(2,3,3,3-tetrachloropropyl)ether (S-421), N-(2-ethylhexyl)bicyclo[2.2.1]hept-5-ene-2,3-dicarboximide (MGK-264) and α-[2-(2-butoxyethoxy)ethoxy]-4,5-methylenedioxy-2-propyltoluene (piperonyl butoxide).

The present invention will be further illustrated in detail by the following Production Examples, Formulation Examples and Test Examples but the present invention is not limited thereto.

First, the production of the compound of the present invention will be illustrated.

PRODUCTION EXAMPLE 1

A solution of 0.14 g of potassium tert-butoxide in 1 ml of tetrahydrofuran was added dropwise to a mixture of 0.35 g of 2,3,5,6-tetrafluoro-4-methoxymethylbenzyl (1R,3S)-2,2-dimethyl-3-formylcyclopropanecarboxylate, 0.21 g of diethyl(chlorocyanomethyl)phosphonate and 5 ml of anhydrous tetrahydrofuran with ice-cooling under a nitrogen atmosphere. After stirring with ice-cooling for 15 minutes, the reaction mixture was poured into a saturated saline solution, and the mixture was extracted with ethyl acetate. The organic layer was dried over anhydrous magnesium sulfate and then filtered, and the filtrate was concentrated under reduced pressure. The residue was subjected to silica gel column chromatography to obtain 0.13 g of 2,3,5,6-tetrafluoro-4-methoxymethylbenzyl (1R,3S)-3-((Z)-2-chloro-2-cyanovinyl)-2,2-dimethylcyclopropanecarboxylate represented by the formula (1):

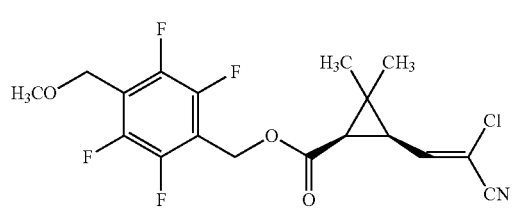

(1)

(hereinafter, referred to as the compound (1) of the present invention) and 0.05 g of 2,3,5,6-tetrafluoro-4-methoxymethylbenzyl (1R,3S)-3-((E)-2-chloro-2-cyanovinyl)-2,2-dimethylcyclopropanecarboxylate represented by the formula (2):

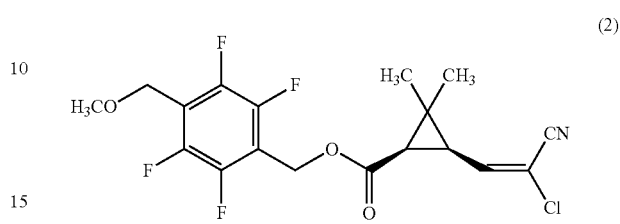

(2)

(hereinafter, referred to as the compound (2) of the present invention).

The compound (1) of the present invention
$^1$H-NMR (CDCl$_3$, TMS) δ (ppm): 7.04 (1H, d), 5.24 (2H, dd), 4.59 (2H, t), 3.41 (3H, s), 2.21 (1H, dd), 2.05 (1H, d), 1.32 (3H, s), 1.30 (3H, s)

The compound of the present invention (2)
$^1$H-NMR (CDCl$_3$, TMS) δ (ppm): 7.09 (1H, d), 5.24 (2H, dd), 4.59 (2H, t), 3.41 (3H, s), 2.25 (1H, dd), 2.07 (1H, d), 1.31 (3H, s), 1.30 (3H, s)

PRODUCTION EXAMPLE 2

A solution of 0.27 g of potassium tert-butoxide in 2 ml of tetrahydrofuran was added dropwise to a mixture of 0.70 g of 2,3,5,6-tetrafluoro-4-methoxymethylbenzyl (1R,3R)-2,2-dimethyl-3-formylcyclopropanecarboxylate, 0.42 g of diethyl(chlorocyanomethyl)phosphonate and 5 ml of anhydrous tetrahydrofuran with ice-cooling under a nitrogen atmosphere. After stirring with ice-cooling for 15 minutes, the reaction mixture was poured into a saturated saline solution and the mixture was extracted with ethyl acetate. The organic layer was dried over anhydrous magnesium sulfate and then filtered, and the filtrate was concentrated under reduced pressure. The residue was subject to silica gel column chromatography to obtain 0.03 g of 2,3,5,6-tetrafluoro-4-methoxymethylbenzyl (1R,3R)-3-((Z)-2-chloro-2-cyanovinyl)-2,2-dimethylcyclopropanecarboxylate represented by the formula (3):

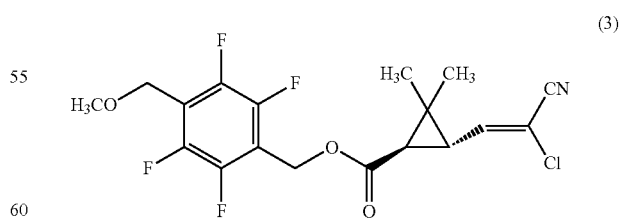

(3)

(hereinafter referred to as the compound (3) of the present invention) and 0.02 g of 2,3,5,6-tetrafluoro-4-methoxymethylbenzyl (1R,3R)-3-((E)-2-chloro-2-cyanovinyl)-2,2-dimethylcyclopropanecarboxylate represented by the formula (4):

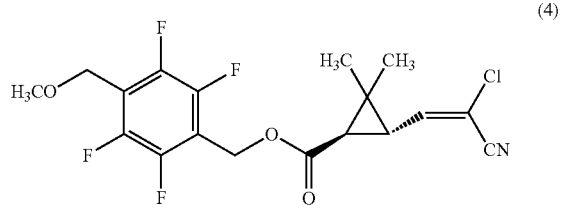

(hereinafter referred to as the compound (4) of the present invention).

The compound (3) of the present invention
$^1$H-NMR (CDCl$_3$, TMS) δ (ppm): 6.30 (1H, d), 5.27 (2H, s), 4.59 (2H, s), 3.41 (3H, s), 2.50 (1H, dd), 1.88 (1H, d), 1.34 (3H, s), 1.25 (3H, s)

The compound (4) of the present invention
$^1$H-NMR (CDCl$_3$, TMS) δ (ppm): 6.23 (1H, d), 5.26 (2H, s), 4.59 (2H, s), 3.41 (3H, s), 2.45 (1H, dd), 1.85 (1H, d), 1.34 (3H, s), 1.25 (3H, s)

Next, the formulation of the pest control composition will be illustrated. All "parts" are by weight.

FORMULATION EXAMPLE 1

In 65 parts of xylene, 20 parts of each of the compounds (1) to (4) of the present invention is dissolved, and 15 parts of SORPOL 3005X (a registered trademark of TOHO Chemical Industry Co., Ltd.) is added thereto and thoroughly mixed with stirring to obtain an emulsion.

FORMULATION EXAMPLE 2

To 40 parts of each of the compounds (1) to (4) of the present invention is added 5 parts of SORPOL 3005× and the mixture is thoroughly mixed, and 32 parts of CARPLEX #80 (synthetic hydrated silicon oxide, a registered trademark of SHIONOGI & CO., LTD.) and 23 parts of 300-mesh diatomaceous earth are added thereto, followed by mixing with stirring by a mixer to obtain wettable powder.

FORMULATION EXAMPLE 3

A mixture of 1.5 parts of each of the compounds (1) to (4) of the present invention, 1 part of TOKUSIL GUN (synthetic hydrated silicon oxide, manufactured by Tokuyama Corporation), 2 parts of REAX 85A (sodium lignin sulfonate, manufactured by WestVaco Chemicals), 30 parts of bentonite FUJI (bentonite, manufactured by Houjun) and 65.5 parts of SHOUKOUZAN A clay (kaoline clay, manufactured by Shoukouzan Kougyousho) is pulverized, and water is added thereto. The mixture is thoroughly kneaded, granulated by an extruding granulator, and then dried to obtain 1.5% granules.

FORMULATION EXAMPLE 4

To a mixture of 10 parts of each of the compounds (1) to (4) of the present invention, 10 parts of phenylxylylethane and 0.5 part of SUMIDUR L-75 (tolylene diisocyanate, manufactured by Sumika Bayer Urethane Co., Ltd.) is added 20 parts of 10% aqueous solution of gum arabic, and the mixture is stirred with a homomixer to obtain emulsion with an average particle diameter of 20 μm. To the emulsion, 2 parts of ethylene glycol is added and the mixture is further stirred in a warm bath at a temperature of 60° C. for 24 hours to obtain microcapsule slurry. On the other hand, 0.2 part of xanthan gum and 1.0 part of VEEGUM R (aluminum magnesium silicate, manufactured by Sanyo Chemical Industries, Ltd.) are dispersed in 56.3 parts of ion-exchanged water to obtain a thickener solution. Then, 42.5 parts of the above-mentioned microcapsule slurry and 57.5 parts of the above-mentioned thickener solution are mixed to obtain a microcapsule formulation.

FORMULATION EXAMPLE 5

A mixture of 10 parts of each of the compounds (1) to (4) of the present invention and 10 parts of phenylxylylethane is added to 20 parts of a 10% aqueous solution of polyethylene glycol, and the mixture is stirred by a homomixer to obtain an emulsion with an average particle diameter of 3 μm. On the other hand, 0.2 part of xanthan gum and 1.0 part of VEEGUM R (aluminum magnesium silicate, manufactured by Sanyo Chemical Industries, Ltd.) are dispersed in 58.8 parts of ion-exchanged water to obtain a thickener solution. Then, 40 parts of the above-mentioned emulsion solution and 60 parts of the above-mentioned thickener solution are mixed to obtain a flowable type pesticide.

FORMULATION EXAMPLE 6

To 5 parts of each of the compounds (1) to (4) of the present invention, 3 parts of CARPLEX #80 (synthetic hydrated silicon oxide, a registered trademark of SHIONOGI & CO., LTD.), 0.3 part of PAP (a mixture of monoisopropyl phosphate and diisopropyl phosphate) and 91.7 parts of talc (300 mesh) are added and the mixture is stirred by a mixer to obtain a dusting powder.

FORMULATION EXAMPLE 7

A solution of 0.1 part of each of the compounds (1) to (4) of the present invention in 10 parts of dichloromethane is mixed with 89.9 parts of deodorized kerosine to obtain an oil-based formulation.

FORMULATION EXAMPLE 8

A solution of 1 part of each of the compounds (1) to (4) of the present invention, 5 parts of dichloromethane and 34 parts of deodorized kerosine is filled into an aerosol container and a valve portion is installed. Then, 60 parts of power propellant (liquefied petroleum gas) is filled therein under pressure through the valve portion to obtain an oil-based aerosol formulation.

FORMULATION EXAMPLE 9

A solution of 0.6 part of each of the compounds (1) to (4) of the present invention, 5 parts of xylene, 3.4 parts of deodorized kerosine and 1 part of ATOMOS 300 (emulsifier, a registered trademark of Atlas Chemical) is filled into an aerosol container and a valve portion is installed. Then, 50 parts of water, and 40 parts of power propellant (liquefied petroleum gas) are filled therein under pressure through the valve portion to obtain an aqueous aerosol formulation.

FORMULATION EXAMPLE 10

A solution of 0.3 g of each of the compounds (1) to (4) of the present invention in 20 ml of acetone is uniformly mixed with stirring with 99.7 g of a base material for a coil (obtained by mixing Tabu powder, Pyrethrum marc and wooden powder at a ratio of 4:3:3). Then, 100 ml of water is added thereto, and the mixture is thoroughly kneaded, dried and molded to obtain an insecticidal coil.

FORMULATION EXAMPLE 11

A mixture of 0.8 g of each of the compounds (1) to (4) of the present invention and 0.4 g of piperonyl butoxide is dissolved in acetone and the total volume is adjusted to 10 ml with acetone. Then, 0.5 ml of this solution is uniformly impregnated into a base material for an insecticidal mat for electric heating (a plate obtained by hardening fibrils of a mixture of cotton linters and pulp) having a size of 2.5 cm×1.5 cm and a thickness of 0.3 cm to obtain an insecticidal mat for electric heating.

FORMULATION EXAMPLE 12

A solution of 3 parts of each of the compounds (1) to (4) of the present invention in 97 parts of deodorized kerosine is poured into a vessel made of vinyl chloride. A liquid absorptive core whose upper part can be heated by a heater (an inorganic pulverized powder is hardened with a binder and sintered) is inserted thereinto to obtain a part to be used for a liquid absorptive core type thermal transpiring apparatus.

FORMULATION EXAMPLE 13

A solution of 100 mg of each of the compounds (1) to (4) of the present invention in an appropriate amount of acetone is impregnated into a porous ceramic plate having a size of 4.0 cm×4.0 cm and a thickness of 1.2 cm to obtain a thermal fumigant.

FORMULATION EXAMPLE 14

A solution of 100 μg of each of the compounds (1) to (4) of the present invention in an appropriate amount of acetone is uniformly applied to filter paper having a size of 2 cm×2 cm and a thickness of 0.3 mm, and air-dried to remove acetone and obtain a volatile agent for using at room temperature.

The following Test Examples will illustrate that the compounds of the present invention are effective as an effective ingredient of a pest control composition.

TEST EXAMPLE 1

Each of the compositions of the compounds (1), (2), (3) and (4) of the present invention obtained by Formulation Example 7 was diluted with mixed solvent of dichloromethane/deodorized kerosine=1/9 (w/w) so that the effective ingredient concentration became 0.1% (w/v) to prepare a test solution.

Ten housefly imagos (each 5 male and 5 female) were released in a polyethylene cup (a base diameter of 10.6 cm) to cover with a 16-mesh nylon bristle. The polyethylene cup was placed at the bottom of a test container (a size of 46 cm×46 cm and a height of 70 cm), and 0.5 ml of the test solution was sprayed from a height of 30 cm above the top face of the polyethylene cup at a spray pressure of 0.9 kg/cm² with a spray gun. The cup was taken out of the test container immediately after spraying to count the number of dead houseflies one day later (two repetitions).

As a result, the lethal rate of houseflies tested was 90% or more by the treatment with each of the compounds (1), (2), (3) and (4) of the present invention (average of the two repetitions).

TEST EXAMPLE 2

Each of the compositions of the compounds (1) and (2) of the present invention obtained by Formulation Example 7 was diluted with mixed liquid of dichloromethane/deodorized kerosine=1/9 (w/w) so that the effective ingredient concentration became 0.00625% (w/v) to prepare a test solution.

Ten houseflies were released in a cubic chamber having a side of 70 cm to spray 0.7 ml of the above-mentioned oil-based preparation into the chamber through a small window on the side face of the chamber at a spray pressure of 0.9 kg/cm² with a spray gun. Then, the number of houseflies knocked down was counted with time until 10 minutes later (two repetitions each). The effect was evaluated with 4 grades of ⊙ to × as described below by means of a $KT_{50}$ value calculated from the obtained results.

As a control test, the similar tests were performed by using as comparative reference compounds 2,3,5,6-tetrafluoro-4-methoxymethylbenzyl (1R,3S)-3-((E)-2-cyano-2-fluorovinyl)-2,2-dimethylcyclopropanecarboxylate

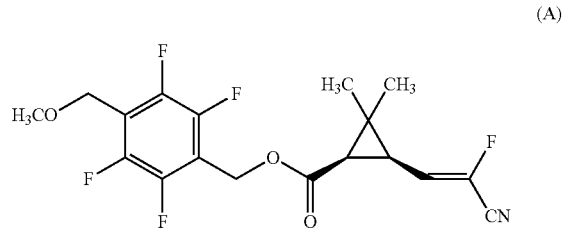

(A)

(hereinafter referred to as control compound (A)) and 2,3,5,6-tetrafluoro-4-methoxymethylbenzyl (1R,3S)-3-((Z)-2-cyano-2-fluorovinyl)-2,2-dimethylcyclopropanecarboxylate

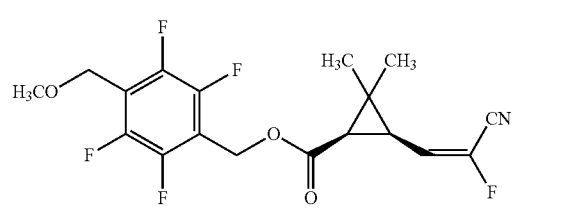

(B)

(hereinafter referred to as control compound (B)) described in U.S. Pat. No. 5,135,951.

The results of each test are shown in Table 1.

TABLE 1

| Test compound | Concentration (w/v) | Efficacy |
|---|---|---|
| The compound (1) of the present invention | 0.00625 | ○ |
| The compound (2) of the present invention | 0.00625 | ⊙ |
| control compound (A) | 0.00625 | X |
| control compound (B) | 0.00625 | Δ |

⊙: $KT_{50}$ value is less than 2 minutes
○: $KT_{50}$ value is 2 minutes or more and less than 3 minutes
Δ: $KT_{50}$ value is 3 minutes or more and less than 4 minutes
X: $KT_{50}$ value is 4 minutes or more

INDUSTRIAL APPLICATION

As described hereinabove, the compound of the present invention has an excellent pest control effect and therefore is useful as an effective ingredient of a pest control composition.

The invention claimed is:

1. An ester compound represented by the formula (I):

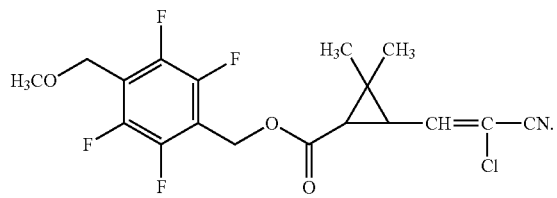

(I)

2. A pest control composition comprising an ester compound represented by the formula (I):

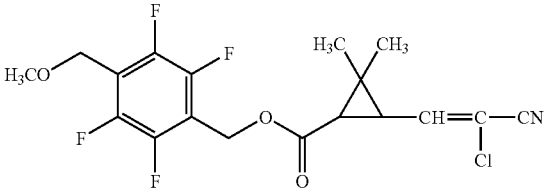

(I)

as an effective ingredient.

3. A pest control method which comprises applying an effective amount of an ester compound represented by the formula (I):

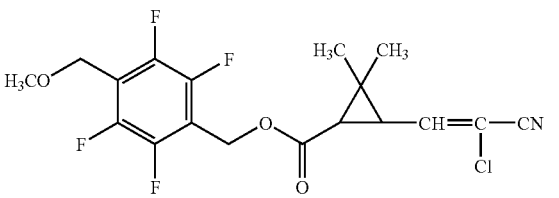

(I)

to pests or a habitat of pests.

* * * * *